US012712106B2

(12) United States Patent
Verheyen et al.

(10) Patent No.: US 12,712,106 B2
(45) Date of Patent: Aug. 18, 2026

(54) MAGNETIC PARTICLE AND METHOD

(71) Applicant: Cambridge Enterprise Limited, Cambridge (GB)

(72) Inventors: Jeroen Verheyen, Cambridge (GB); Tarun Vemulkar, Cambridge (GB); Russell Cowburn, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 693 days.

(21) Appl. No.: 18/122,307

(22) Filed: Mar. 16, 2023

(65) Prior Publication Data

US 2023/0290556 A1 Sep. 14, 2023

Related U.S. Application Data

(63) Continuation of application No. 17/291,563, filed as application No. PCT/GB2019/053188 on Nov. 11, 2019, now Pat. No. 11,640,865.

(30) Foreign Application Priority Data

Nov. 12, 2018 (GB) ..................................... 1818421

(51) Int. Cl.
*H01F 10/26* (2006.01)
*G01N 33/543* (2006.01)
*H01F 41/34* (2006.01)

(52) U.S. Cl.
CPC ..... *H01F 10/265* (2013.01); *G01N 33/54326* (2013.01); *H01F 41/34* (2013.01)

(58) Field of Classification Search
None
See application file for complete search history.

(56) References Cited

U.S. PATENT DOCUMENTS

| | | | |
|---|---|---|---|
| 5,932,097 | A | 8/1999 | Wilson |
| 6,103,538 | A | 8/2000 | Kotsugai |
| 8,617,798 | B2 | 12/2013 | Mason et al. |
| 8,848,194 | B2 | 9/2014 | Walters et al. |
| 9,040,310 | B2 | 5/2015 | Ashworth-Sharpe et al. |
| 9,715,159 | B1 | 7/2017 | Akselrod et al. |
| 2010/0035061 | A1 | 2/2010 | Mason et al. |
| 2012/0228386 | A1* | 9/2012 | Wu .................. B01L 3/502761 235/488 |
| 2013/0052343 | A1 | 2/2013 | Dieny et al. |
| 2014/0141085 | A1 | 5/2014 | Barashkov et al. |
| 2016/0025744 | A1 | 1/2016 | Feldman et al. |
| 2017/0271067 | A1 | 9/2017 | Raksha et al. |
| 2017/0362645 | A1 | 12/2017 | Prins et al. |
| 2018/0258513 | A1 | 9/2018 | Suetsuna et al. |
| 2019/0307903 | A1 | 10/2019 | Morel et al. |

FOREIGN PATENT DOCUMENTS

| | | | |
|---|---|---|---|
| EP | 1662256 | A1 | 5/2006 |
| JP | 11230965 | | 8/1999 |
| JP | 2001332421 | A | 11/2001 |
| JP | 2005538233 | A | 12/2005 |
| JP | 2013505568 | A | 2/2013 |
| JP | 2016501286 | A | 1/2016 |
| KR | 20150074647 | A | 7/2015 |
| WO | 2004003231 | A3 | 1/2004 |
| WO | 2013078452 | A9 | 5/2013 |

OTHER PUBLICATIONS

English Language Office Action mailing date Mar. 7, 2025 corresponding to EP Patent Application No. 19804806.8.
English Language Office Action mailing date Sep. 25, 2025 corresponding to EP Patent Application No. 19804806.8.
Japanese Office Action from Application No. 2021-525640 and it's English translation.
Vemulkar et al., "Highly tunable perpendicularly magnetized synthetic antiferromagnets for biotechnology applications", DOI: dx.doi.org/10.1063/1.4926336.
International Preliminary Report on Patentability, May 11, 2021.
Vermulkar et al. "Highly tunable perpendicularly magnetized synthetic antiferromagnets for biotechnology applications", Appl. Phys. Lett., 107, 2015.
Mansell et al. "Magnetic particles with perpendicular anisotropy for mechanical cancer cell destruction", Scientific Reports, 7:4257; 2017.
Intemational Search Report and Written Opinion, mailed Feb. 10, 2020.
Vermulkar et al. "The mechanical response in a fluid of synthetic antiferromagnetic and ferrimagnetic microdiscs with perpendicular magnetic anisotropy", Applied Physics Letters, vol. 110, No. 4, Jan. 24, 2017.
GB Search Report, dated Apr. 29, 2019.
Pregibon et al; "Multifunctional Encoded Particles for High-Throughput Biomolecule Analysis", Science, vol. 315, Mar. 9, 2007.
Appleyard et al; "Bar-coded hydrogel microparticles for protein dedection: synthesis, assay and scanning", Nature Protocols, vol. 6, No. 11, Oct. 20, 2011.

* cited by examiner

*Primary Examiner* — Ann Montgomery
(74) *Attorney, Agent, or Firm* — Thomas Horstemeyer, LLP

(57) ABSTRACT

A magnetic particle (30, 70) has a layered structure (6, 56) between a top surface of the particle and an opposed bottom surface of the particle. Layers of the structure include one or more non-magnetic layer(s) and one or more magnetized layer(s). The ratio of a lateral dimension of the one or more magnetized layers to the aggregate thickness of the magnetized layer or layers is greater than 500. A plurality of such magnetic particles (30, 70) can be functionalised and marked with readable codes (16, 66) corresponding to the functionalisation, for use for performing assays such as bioassays.

18 Claims, 9 Drawing Sheets

MAGNETIC PARTICLE AND METHOD

CROSS-REFERENCE TO RELATED APPLICATION

This application is a continuation of, and claims priority to and the benefit of, copending U.S. patent application Ser. No. 17/291,563, entitled "MAGNETIC PARTICLE AND METHOD" and filed on May 5, 2021, which claims priority to and the benefit of PCT Application No. PCT/GB2019/053188, filed on Nov. 11, 2019 and entitled "MAGNETIC PARTICLE AND METHOD," which claims priority to and the benefit of GB Patent Application No. 1818421.8, filed on Nov. 12, 2018 and entitled "MAGNETIC PARTICLE AND METHOD." The entire content of each of these applications is incorporated by reference as if set forth herein in their entireties.

The invention relates to a magnetic particle, and methods of making and using magnetic particles.

BACKGROUND ART

Techniques for using an applied magnetic field to exert mechanical forces on individual magnetic particles have been leveraged in various biotechnology applications.

One important commercial use for magnetic nanoparticles and microparticles is currently for bioassays, to isolate and identify biological molecules. Superparamagnetic iron-oxide nanoparticles (SPIONs) are conventionally used for this commercial range of applications, because they offer the property of migrating towards an external magnetic field source. This enables particles to be steered by the application of an external magnetic field towards a desired location for reading the assay information. These particles are nanoparticles (5-20 nm in diameter) made by colloidal chemistry methods. The size of these particles is limited by the fact that if the particles are made larger, beyond approximately 20 nm, the particles become ferromagnetic and the effect of the stray magnetic field of one particle on other particles disadvantageously leads to magnetic agglomeration of the particles, which prevents their use in bioassays.

Technologists developing magnetic particles need to optimize the magnetic properties of the particles for each application. Conventionally, it is accepted that a highly-desirable property for magnetic nanoparticles for all of these various applications, including the bioassay applications, is a net-zero magnetization remanent state in order to avoid particle agglomeration.

A net-zero-magnetization remanent state means that in the absence of a magnetic field, the magnetic particles have no net magnetic moment and no external stray field. In use, magnetic particles are typically suspended in a liquid or fluid medium and are free to move within that medium. For particles with non-zero remanent moments, the particles' stray fields may interact and cause the particles to agglomerate, or to clump together. This is undesirable because the purpose of using magnetic particles in biotechnology applications is to be able to steer, or direct the motion of, particles suspended in a liquid or fluid medium by applying an external magnetic field. If the magnetic particles agglomerate, then this cannot be achieved.

In addition, it is understood in the art that to ensure that small magnetic fields from the environment cannot cause agglomeration by inducing magnetic moments in magnetic particles, the particles with zero net magnetization remanent state should also have a low susceptibility at small fields.

Furthermore, if particles with a high susceptibility are used, then after an applied field has been applied to direct or move the particles in a desired manner, then particles which have agglomerated during the application of the field stay agglomerated once the applied field is removed. It is understood by the skilled person that this should also be avoided in magnetic particles for biotechnology applications.

Thus the prior work in the art of creating magnetic nanoparticles that do not agglomerate has focused entirely on systems that have a zero net remanent magnetization state, preferably with low magnetic susceptibility. This includes a variety of systems such as superparamagnetic nanoparticles, magnetic vortex micro and nanoparticles, and micro and nanoparticles utilizing antiferromagnetic coupling to create opposing magnetization configurations between adjacent magnetic layers in the particle.

An important biotechnology application is to carry out multiplexed immunoassays of biological samples. The accurate quantification of proteins in a biological sample is of significant importance for both research and clinical diagnostic applications. A multiplexed immunoassay simultaneously quantifies a plurality of different proteins in a given sample. Analysing protein fingerprints of samples in this way has the potential to accelerate research and to enable improved diagnostics. In response to this market need, multiplexed assay systems such as Luminex®, Firefly® and Fireplex® have been developed. These systems use individual particle sets in which each particle is coated with a capture antibody qualified for one specific analyte. Multiple sets of analyte-specific particles can then be combined to detect and quantify multiple targets simultaneously through the use of detection antibodies marked with fluorescent labels. The Luminex® system is based on polystyrene or paramagnetic microspheres, or beads, that are internally dyed with red and infrared fluorophores of differing intensities to allow the differentiation of one set of beads from another. The Firefly® and Fireplex® systems also use fluorophores to allow differentiation of one particle set from another, but in this case the particles are in the form of rods coded by applying a different fluorophore at each end.

Measurement of the fluorophores again aims to distinguish one rod from another. However, in practice these systems suffer from limited multiplexing (limited number of different proteins that can be identified) due to limited ability to distinguish with certainty between the channels of the multiplex in assay results.

SUMMARY OF INVENTION

The invention provides a magnetic particle, a plurality of magnetic particles for performing assays, and a method for performing an assay using the magnetic particle(s), as defined in the appended independent claims to which reference should now be made. Preferred or advantageous features of the invention are set out in dependent subclaims.

In a first aspect the invention may thus provide a magnetic particle, comprising a layered structure between a top surface of the particle and an opposed bottom surface of the particle, the layer or layers including one or more magnetized layers. The ratio of a lateral dimension of the one or more magnetized layers to the thickness, or aggregate or effective thickness, of the magnetized layer or layers is greater than 500. In other words, the aspect ratio of a cross section of the magnetized layer or layers may be more than 500. In preferred embodiments, the ratio may be higher, for example being greater than 800 or greater than 1000 or 1500 or 2000.

The particle may further comprise a non-magnetic layer, which may advantageously provide mechanical support to the magnetic layer, and may determine physical characteristics of the particle such as its mechanical properties and its density.

The particle may comprise one magnetized layer, or it may comprise more than one such layer. If it comprises two or more magnetized layers, then layers may be adjacent to each other, or in contact with each other, or they may be spaced from each other with non-magnetic material in between. The aggregate thickness, or total thickness, of the magnetically-remanent layers in a particle having more than one magnetized layer may be the sum of the thicknesses of those magnetic layers, not including any non-magnetic layers in between them. In some embodiments, the layered structure may comprise many magnetized layers and/or many layers of a non-magnetic material.

A magnetized, or magnetic, layer may for example comprise any suitable magnetic material or materials, such as a ferromagnetic material, element or alloy, or a composite of superparamagnetic nanoparticles.

The particle is preferably substantially flat in shape, comprising one or more substantially flat layers of magnetic and/or non-magnetic materials stacked on top of one another. The layers are preferably of substantially the same shape and size as each other, each having the same lateral shape and size as the particle itself. However, the shape and structure of the particle may vary from this as described further below.

The particle may have a zero or a non-zero magnetic remanence. However, the inventors have found that even if a particle has non-zero magnetic remanence, then the shape and structure of a particle embodying the invention displays an unexpectedly-low stray field at the surfaces of the particle, so that a plurality of the particles suspended in a fluid or liquid medium may advantageously not aggregate or clump. Surprisingly, the inventors have found that this is the case whether or not the particles are fully magnetically remanent.

In a preferred embodiment of the invention, when an external field is applied the particle has a sufficient magnetic moment for the external field to apply a desired force to the particle. The desired force may depend on the application of the particle (such as in a bioassay with the particle suspended in a fluid medium). In practical implementations, the applied external field is typically less than 2 T, or 1 T or 0.5 T, and may typically be greater than 0.05 T or 0.1 T or 0.25 T.

For example, in a bio- or chemical assay, it may be desired to use the external field to steer the particle within a fluid medium. The magnetic moment may be due to magnetization of the particle itself, or it may be induced in the particle by the external field. It is important, however, for the particle to contain sufficient magnetic material to enable the desired force to be generated.

The magnetic moment that can be generated by an external field applied to a particle may depend on the total volume V of magnetic material in the particle multiplied by that material's magnetization $M_s$. Thus, the value of $V \cdot M_S$ for a particle embodying the invention is preferably greater than a predetermined value, such as $10^{-18}$ J/T or $5\times10^{-18}$ J/T or $10^{-17}$ J/T.

The inventors have found that the physical distribution of the magnetic material within the particle may determine the stray field near the particle, and therefore the tendency of particles to interact with each other and/or to agglomerate. The inventors have found that distributing the magnetic material in the form of a layer or layers (preferably parallel layers) having a cross section with high aspect ratio AR may generate an advantageously low stray field. This preferred particle geometry may advantageously provide particles with low stray field and little or no tendency to agglomerate.

To evaluate this particle geometry in a more quantitative manner, the inventors suggest that in preferred particles, the parameter $AR/M_S^2$ of the magnetic layer or layers (with AR being a dimensionless ratio and $M_S$ being the magnetization of the magnetic material in the magnetic layer or layers measured in A/m (1000 A/m is equivalent to 1 emu/cm$^3$)) is preferably greater than $8\times10^{-10}$ m$^{-2}$/A$^{-2}$, or 1.2×10−9 m$^{-2}$/A$^{-2}$ or 8×10−9 m$^{-2}$/A$^{-2}$.

Alternatively, or in addition, the inventors have determined that the parameter $AR/M_S$ is preferably greater than 1×10−3 m$^{-1}$/A$^{-1}$ or 3×10−3 m$^{-1}$/A$^{-1}$ or 5×10−3 m$^{-1}$/A$^{-1}$.

These limits correspond to a stray field of less than about 2500 A/m (30 Oe) at 10 times the layer thickness above or below the layer. Depending on the application and environment of the particles, this level of stray field may advantageously prevent agglomeration.

When assessing the value of AR for a particle structure, AR may be a lateral dimension of a cross section of the structure divided by a thickness of the structure. For a layer of magnetic material, the lateral dimension may be the minimum lateral dimension of the layer or, if the shape of the layer is more complex, then it may be preferable to consider an average lateral dimension of the layer. If the thickness of the layer is constant, then that thickness can be used for the calculation of AR. If the thickness of the layer varies, then an average thickness can be used.

It may be appropriate to use equivalent lateral and thickness dimensions of the particle itself to calculate AR, for example if the magnetic material spans the full lateral dimension of the particle, and particularly if the thickness of the particle is sufficiently similar to the thickness of the magnetized layer or layers, such as less than 10 times, or 5 times, the thickness of the magnetized layer or layers. In this approach to evaluating AR/Ms, as well as using the AR value for the particle, the value of $M_S$ may be modified by calculating a diluted $M_S$ value, being the $M_S$ of the magnetized material in the particle multiplied by the volume ratio of non-magnetized and magnetized material in the particle.

A particle may comprise multiple magnetized layers, for example in the form of a stack of magnetized layers spaced by layers of non-magnetized material. In such cases, if the magnetized layers are spaced from each other by a sufficiently small distance, such as less than 5, 10 or 20 times the thinnest layer thickness or the average layer thickness, then AR may be evaluated using either the aggregate thickness of the magnetized layers or the distance between the outermost magnetized layers in the stack, including the thickness of any intervening non-magnetic layers.

If a particle comprises multiple layers that span a sufficient proportion of the particle thickness, then AR may be evaluated using the particle thickness.

If a particle comprises multiple layers, an alternative approach to evaluating the thickness for calculating AR may be to calculate a diluted thickness for the magnetized material. If for example, two or more parallel layers of magnetized material of aggregate thickness Tm are separated by layers of non-magnetic material of aggregate thickness Tnm, then the diluted thickness of the magnetized material would be Tm/(Tm+Tnm).

It may also be possible to evaluate AR and Ms (for the calculation of $AR/M_S^2$ or $AR/M_S$) for an entire particle by measurement. If the magnetic moment of a set number of particles of unknown structure but known dimensions is measured (for example using a vibrating-sample magnetometer), the effective $M_S$ may be found using the total particle volume and the total moment per particle. The particle or metallic layer(s) lateral dimension and thickness may be measured directly, for example using microscopy and/or electron microscopy techniques, to evaluate AR.

Particles embodying the invention are preferably planar in shape, with their length and width both being greater than their thickness. Advantageously the length and width of the particle, or two lateral dimensions of the particle measured perpendicular to each other, are similar to each other, or differ from each other by less than about 10%, 30%, 50% or 70%. A particle might typically be in the form of a circular or elliptical or polygonal disc, or a generally flat cuboid with a square or rectangular perimeter.

The magnetic material in a particle preferably extends across substantially the entire lateral dimensions of the particle, in the form of a layer or layers within the particle. The aspect ratio of the magnetic layer or layers can be assessed with reference to the minimum lateral dimension, or an average lateral dimension, of the layer or layers, which may be the same as or smaller than the lateral dimension of the particle. If one magnetized layer is present, then the aspect ratio AR may be the minimum, or an average, lateral dimension of the magnetic layer divided by its thickness (or an average thickness if the thickness varies). If multiple magnetized layers are present, then the aspect ratio AR may be evaluated as the lateral dimension, or an average lateral dimension if different layers have different lateral dimensions, divided by an aggregate thickness of the layers.

In preferred embodiments, the top and bottom surfaces of the particle may be separated by a particle thickness of between 5 nm, or 10 nm or 50 nm or 100 nm, and 100 μm or 50 μm or 5 μm or 1 μm or 500 nm. A minimum lateral dimension of the particle may be greater than 1 μm, and preferably greater than 5 μm or 10 μm, and a maximum lateral dimension may be less than 500 μm or 200 μm or 100 μm or 50 μm. A ratio of the minimum lateral dimension of the particle to the thickness of the particle may be greater than 10 or 20 or 50 and/or less than 2000 or 1000 or 500. In such preferred embodiments, the particle may therefore have a rather flat, high-aspect ratio shape, although other embodiments envisage lower-aspect-ratio particle shapes, and even spherical or cube-shaped particles. Such a lower-aspect-ratio particle may comprise one or more magnetized layer(s) having a higher aspect ratio, as discussed above and herein.

In embodiments comprising more than one magnetized layer, those layers are preferably substantially parallel to each other. In embodiments comprising more than one magnetized layer, those layers preferably have similar shapes and/or areas as each other, and may conveniently overlap with each other, optionally completely overlapping with each other.

The opposed top and bottom surfaces of the particle are advantageously flat, but one or both surfaces may optionally be curved or not flat without affecting the desired property of the particle having a sufficiently small stray field to avoid aggregation. The particle itself may thus be flat or curved. But in each case, the opposed top and bottom surfaces may advantageously be of sufficiently large area to enable features such as readable information, such as readable codes in the form of barcodes or 2D codes, to be applied to the top and/or bottom surfaces so that individual particles or groups of particles (if the particles in a group of particles are similarly marked) can be identified by reading the information. Such information may be applied to the top and/or bottom surfaces, or may be applied beneath the top and/or bottom surfaces, for example beneath a surface layer or layers that is or are sufficiently transparent to allow the codes or information to be read through the surface layer or layers. Further, the top or bottom surfaces may advantageously form suitable substrates for the application of other functionality to the particles, such as biofunctionality or chemical functionality for biotechnological or chemical applications as described herein.

In a preferred embodiment, the shape of the particle may thus be in the form of a thin (low thickness) laterally-extended shape, such as a high-aspect-ratio cuboid or disc. (Aspect ratio refers to the ratio of the minimum lateral dimension, or of an average lateral dimension, to the thickness.) Alternatively, the magnetic particle may be described as being cylindrical in shape, the thickness of the particle being in an axial direction of the cylinder, with the peripheral shape of the cylinder preferably being selected so that it typically has an edge or edges which are convex or straight, advantageously with no re-entrant corners. Preferred peripheral shapes are rectangular or square or circular.

While being of a high-aspect-ratio or cylindrical shape, as described above, it is contemplated that while the particle is preferably flat, with flat top and bottom surfaces, embodiments of the invention may include curved or non-flat particles, or particles with curved or non-flat upper and lower surfaces, while achieving the object of providing non-aggregating magnetic particles.

Preferably, the minimum and maximum lateral dimensions of the magnetic particle differ by less than 90% or less than 70%. In preferred embodiments, the minimum lateral dimension of the particle is greater than 5 μm, and preferably greater than 10 μm, and/or the maximum lateral dimension of the particle is less than 500 μm, and preferably less than 200 μm, 100 μm or 75 μm. These dimensions may be selected by the skilled person depending on the application for which the particles are being used, and requirements such as the desired mechanical strength of the particles.

The layered structure of the magnetic particle advantageously comprises a magnetized layer and a non-magnetic layer. The non-magnetic layer may provide mechanical strength to the particle, and may provide a suitable substrate for the magnetized layer. The non-magnetic layer may thus advantageously comprise a material selected from Al, Ta, Pt, Pd, Ru, Au, Cu, W, MgO, Cr, Ti, Si, Ir, $SiO_2$, SiO, Sn, Ag, polymers, plastics, alloys of these materials, and composites or mixtures comprising these materials.

The particle may comprise two or more layers of non-magnetic material, which may similarly be selected from this group.

The magnetized, or ferromagnetic, layer may be formed from any suitable material, and in preferred embodiments may comprise a material selected for example from metals or metallic alloys such as Fe, Co, Ni, CoFe, CoFeB, FePt, CoNi and NiFe.

The magnetized layer may for example comprise a magnetic multilayer stack of alternating layers of a magnetic material and a noble metal (such as Pt/CoFeB) where the pair is known to provide perpendicular magnetic anisotropy.

The magnetized, layer is preferably an out-of-plane magnetized layer, but may be a differently magnetized layer such as an in-plane magnetized layer.

A high saturated magnetic moment is desirable for the magnetic particles, in order to achieve a rapid response to an external field. The magnetic material is selected to achieve this.

The layered structure of the magnetic particle may comprise more than one layer of non-magnetic material, and/or may contain more than one layer of magnetized material. In a preferred embodiment, the particle may comprise a magnetized layer positioned between two layers of non-magnetic material.

A particle may comprise two or more magnetized layers arranged, in combination, to have zero magnetic remanence in the absence of an applied field. Such a particle may have a magnetic susceptibility such that the application of an external field induces a magnetic moment in the particle. An external field may therefore be applied in order to move or steer the particle, for example through a fluid medium. Advantageously, however, it may not matter whether the particle has a high or low susceptibility because the shape of the particle embodying the invention is such that the stray field around the particle may advantageously be too low to cause particle agglomeration even when the magnetic moment is induced.

In such a particle, the magnetized layer may advantageously be spaced from the top surface of the particle by more than 25% of the particle thickness, and spaced from the bottom surface of the particle by more than 25% of the particle thickness. This structure may advantageously further reduce stray magnetic fields at the opposed top and bottom surfaces of the particle.

Preferably, the magnetized layer may have a thickness, or an average thickness, greater than 0.1 nm, or 0.4, 1.0 or 1.5 nm. Preferably, the thickness of the magnetized layer may be less than 25%, and particularly preferably less than 15% or 10%, of the total thickness of the particle. The particle could comprise only a magnetized layer, if the mechanical strength of the particle were sufficient for a desired application.

The magnetized layer may for example be a thin-film multilayer.

The net magnetic field (the stray field) averaged across the lateral surface at or within a small distance of a top or bottom surface of the particle may preferably be less than 2500 A/m (30 Oe) and particularly preferably less than 800 A/m (1 Oe) or 400 A/m (5 Oe). This field may be measured at the surface, or at a small distance such as 10 nm, 50 nm or 100 nm from the surface, for example by using a magnetic atomic force microscope. The inventors' experiments have indicated that these external, or stray, magnetic fields are sufficiently small to avoid agglomeration of magnetic particles.

Magnetic particles embodying the invention may conveniently be manufactured or fabricated by lithographic processes.

A second aspect of the invention may advantageously provide a magnetic particle having dimensions as described above, but preferably in which a top surface of the particle and an opposed bottom surface of the particle are separated by a particle thickness of between 5 nm and 200 μm, a minimum lateral dimension of the particle is greater than 1 μm, and the ratio of the minimum lateral dimension to the thickness is greater than 10, and in which the particle comprises a layered structure through its thickness, the layers including one or more magnetically-remanent, or magnetized, layer(s) and one or more layer(s) of a non-magnetic material. Such a particle may conveniently be fabricated by a lithographic process, and may comprise one or more of the features of the first aspect of the invention described herein.

In a further aspect of the invention, a top or bottom surface of the particle may carry readable information, such as a readable code. This may be for example a barcode or 2D code. This may allow the particle to be identified remotely by reading the information, for example with a camera and suitable software.

In a preferred embodiment, the magnetic properties of the particle enable a suitable external magnetic field to be applied to steer or move or drive the particle through a fluid medium to a predetermined location for reading the code or information. For example, a particle having a high-aspect-ratio shape with a large top or bottom surface on which a code or information is carried, may be directed so that it is in contact with a substrate or other supporting surface for convenient reading of the code or information.

In a still further aspect of the invention, a top and/or bottom surface of the particle may be functionalised, for example biofunctionalized or chemically functionalised. This may advantageously be in combination with applying readable information to the particle. For example, a top or bottom surface of the particle may carry a readable code and the same or an opposite surface may be functionalised. Further, in a preferred embodiment, a plurality of particles may be provided in which each particle carries readable information corresponding to the functionalisation of that particle.

Such a particle may enable the performance of an assay, such as a bioassay, by providing the particle to a liquid or fluid assay sample and allowing the functionality of the particle to interact with the assay sample, for example with biological molecules or other components of the assay sample. A magnetic field may be applied to steer the particle to a reading position, and an assay result obtained by reading the readable code and measuring the interaction of the particle's functionality with the assay sample.

A multi-channel assay may be performed by providing a plurality of particles in which each particle carries readable information corresponding to the different functionality of that particle. The plurality of particles may contain groups of particles, the particles in each group carrying similar readable information and being similarly functionalised. The plurality of particles can be contacted with a liquid or fluid assay sample, allowing the functionality of the particles to interact with the assay sample. A magnetic field is applied to steer the particles to a reading position, and an assay result obtained by reading the readable information for two or more particles and measuring the respective interaction of the corresponding functionalities of each particle with the assay sample.

The identification of particles using readable information in this way may advantageously provide a multiplexed platform in which the particles can be accurately distinguished from each other. The use of barcodes, or 2D codes, for example may provide a significantly more robust process for identifying different particles than in existing multiplexed assay platforms, with minimum crosstalk between plex channels. In addition, the use of readable information in this way may enable the use of very much larger numbers of multiplex channels than is currently possible. For example, barcoding or 2D codes may enable 1000 plex, or 10,000 plex, or more if desired.

In preferred embodiments, the invention may thus relate to lithographically defined, perpendicularly (or out-of-plane) magnetized particles, advantageously in the form of ferromagnetic microdiscs (microparticles, nanoparticles, microcarriers etc.) for use in biotechnology applications. For example, these particles may be ferromagnetic microparticles or microdiscs (between 1-500 μm, or 1-200 μm, or preferably 5-100 μm, in each lateral dimension, or in two orthogonal lateral dimensions, and between 10 nm and 200

μm, or preferably 20 nm and 10 μm thick) fabricated by photolithography and by the physical vapour deposition of magnetized thin film multilayers. For example, the particles may be circular or square, 40 μm in diameter or side length, and 100 nm thick. Or they may be 100 μm in diameter or side length, and 1 μm thick. The resultant high planar aspect ratio, ultra-thin discs, or microdiscs, (which may be referred to as magnetic carriers (MCs) because of their ability to carry functionalisations such as biofunctional antibodies for diagnostic tools) are ferromagnetic with high magnetic moment. The MCs may be lithographically-defined. The MCs do not agglomerate when suspended in a fluid because the aspect ratio of each magnetic layer (typically 1 nm, or 5 nm, total magnetic layer thickness and tens of μm in lateral size), and magnetization direction perpendicular to the plane of the MC results in a negligible stray magnetic field from each particle.

In preferred forms, the MCs may be characterized by a magnetization direction parallel to the surface normal of the microdisc, as well as coercive magnetization reversal, and a high magnetic anisotropy. These properties may all enable a higher degree of control over their magnetic response and hence their mechanical behaviour in a fluid under the influence of an external magnetic field.

The physical vapour deposition process which is preferably used to fabricate the particles, or MCs, enables sub-nm control in the deposition of the magnetic thin films that form the MCs, and thus offers extreme precision in the engineering in the magnetic properties of the MCs.

This may advantageously enable them to be tailored to different applications. Further, barcodes (or other readable information) may be lithographically added to the surface of MCs, and the surface materials may be chosen for optimal functionalization with molecules of interest.

SPECIFIC EMBODIMENTS AND BEST MODE OF THE INVENTION

Specific embodiments of the invention will now be described by way of example, with reference to the accompanying drawings in which.

Figure 3:
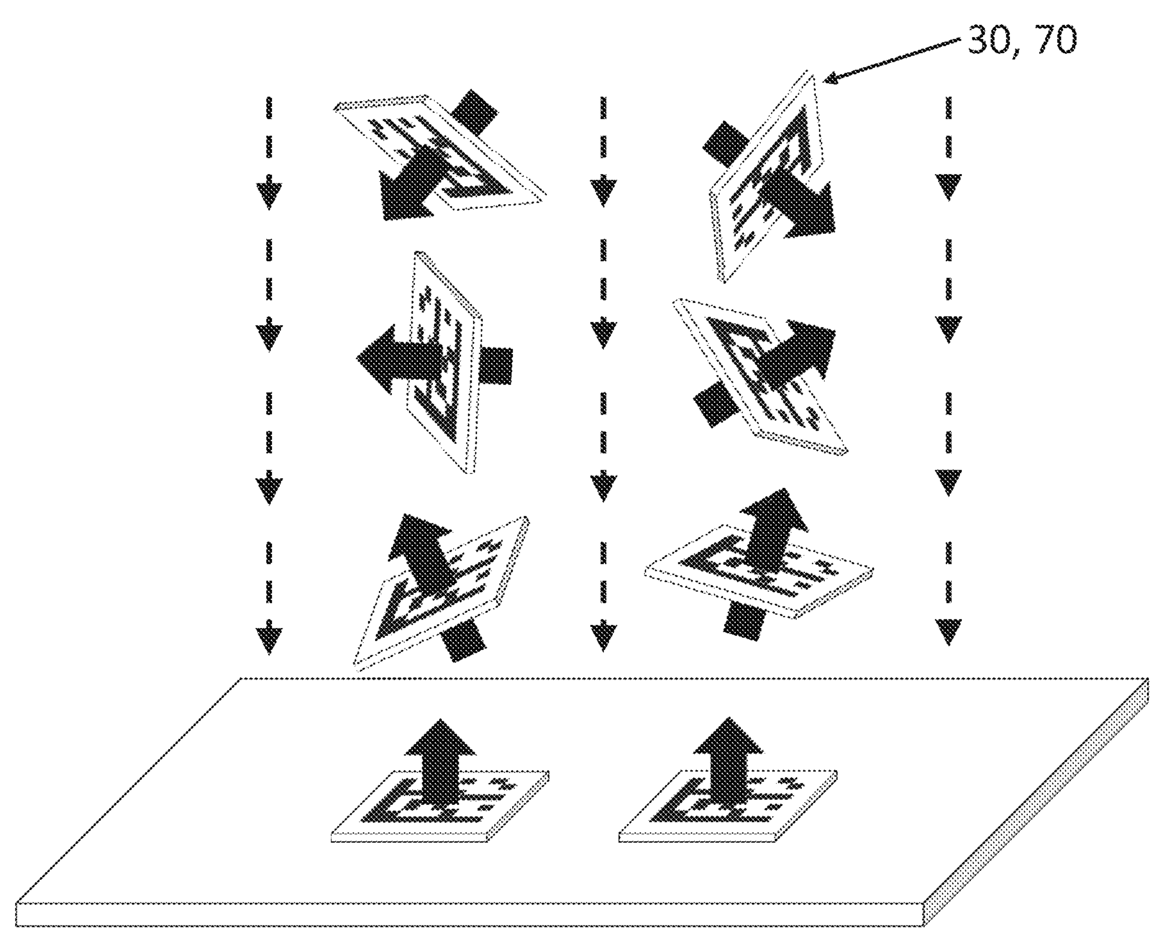
Figure 3:
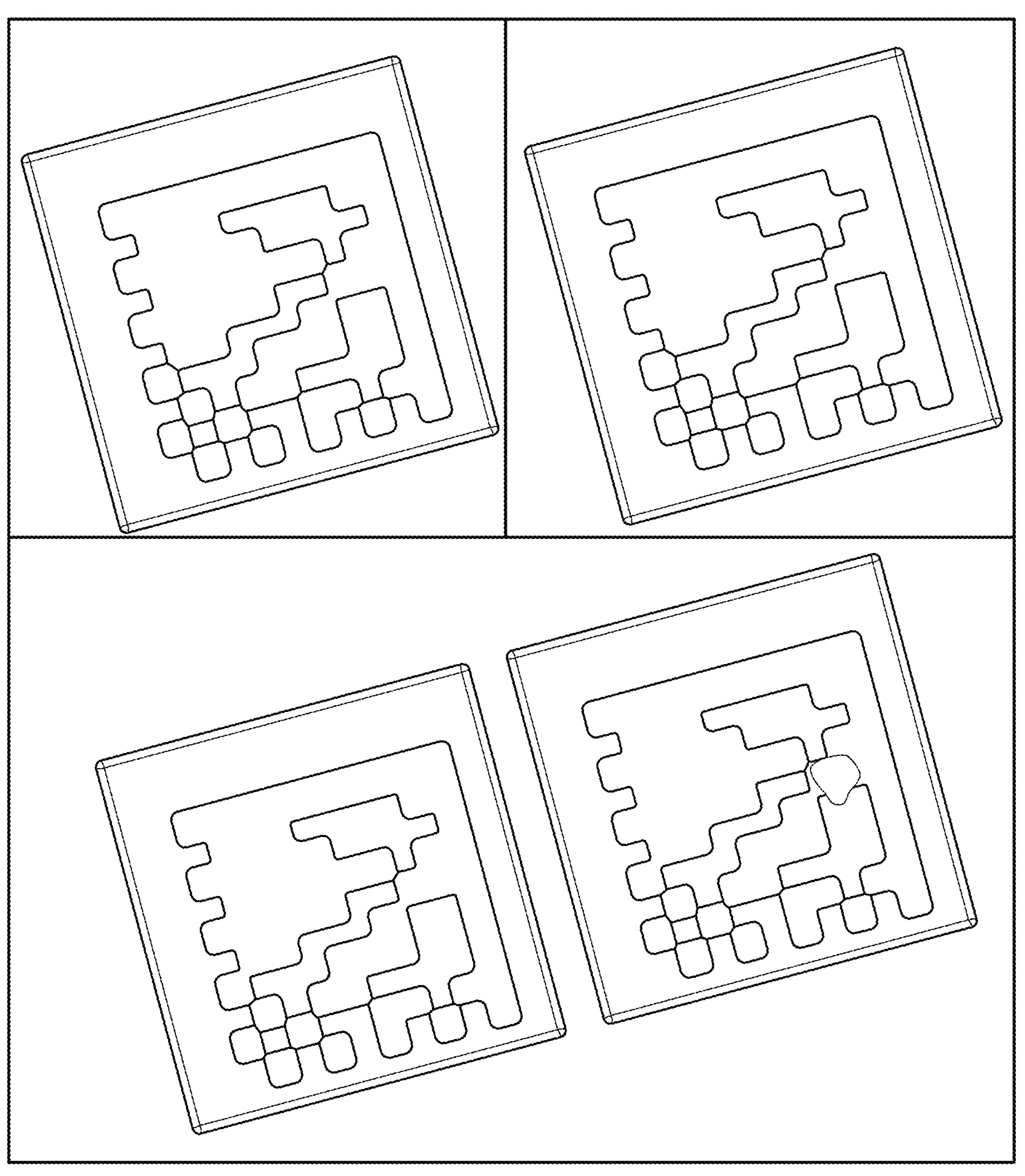
Figure 4:
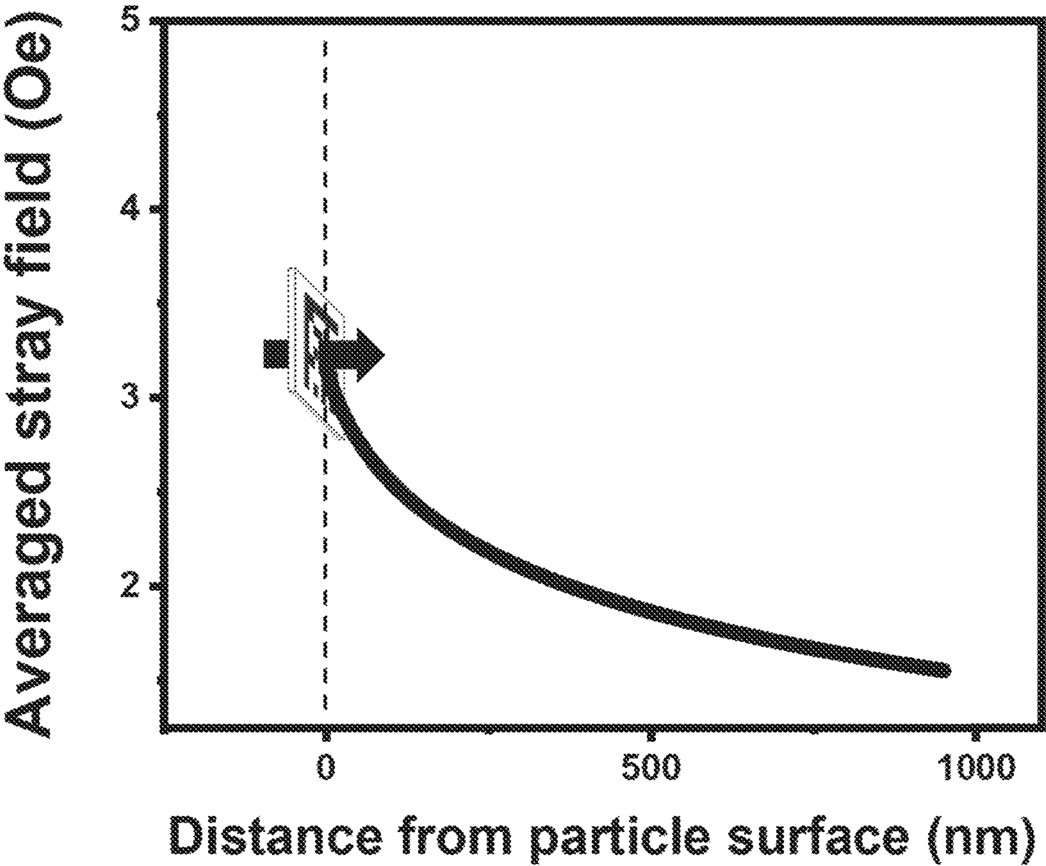
Figure 5:
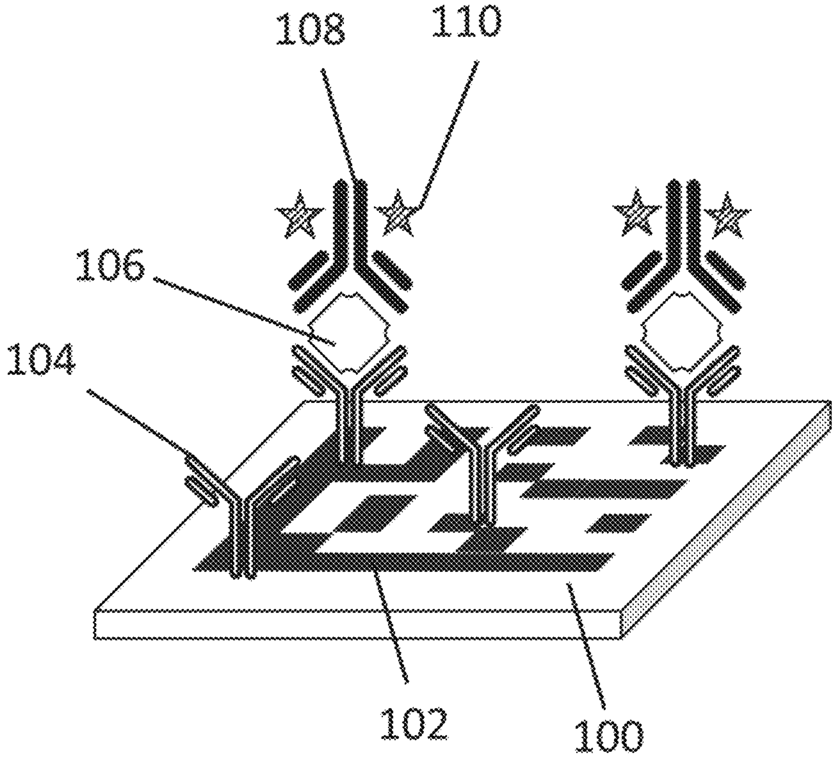
Figure 5:
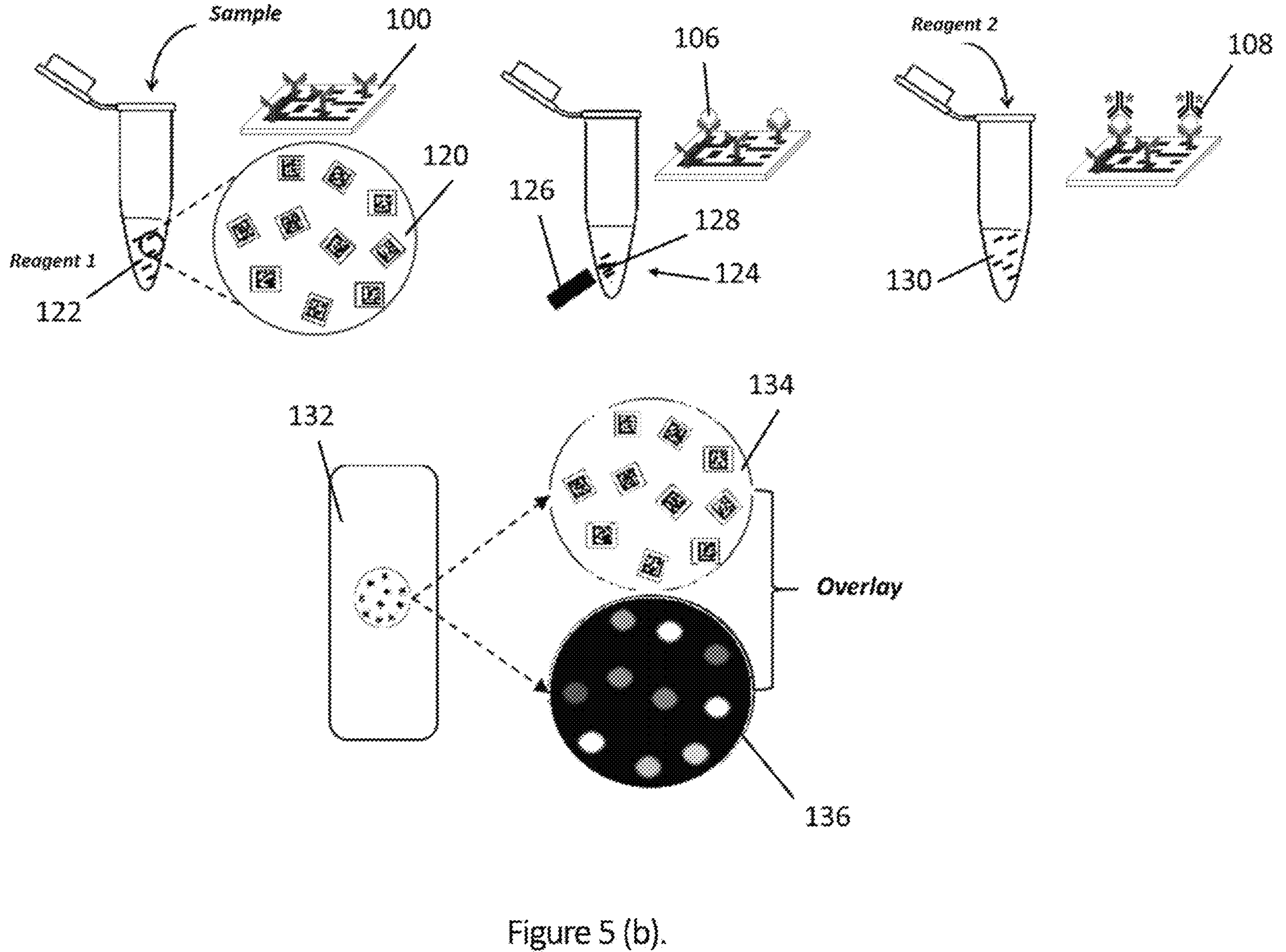

FIGS. 3(*a*) and 3(*b*) illustrate how the readable code and the magnetic states in particles according to the embodiments are linked to ensure that the readable code may always be aligned to an external detector, such as a camera or barcode reader, by an applied magnetic field, and show images of readable codes of particles imaged by a detector;

FIG. 4 illustrates stray field strength as a function of distance from the surface of a particle manufactured according to the embodiments; and FIGS. 5(*a*) and 5(*b*) illustrate a functionalised particle according to a further embodiment of the invention, suitable for a bioassay, and illustrate the use of particles according to the further embodiment of the invention to implement a streamlined multiplex assay.

A specific embodiment of the invention involves the fabrication of high magnetic moment microparticles made from ultrathin perpendicularly-magnetized CoFeB/Pt layers. The high aspect ratio of the shape of these particles results in an extremely low stray magnetic field from each particle, such that the magnetic nanoparticles show no inter-particle interaction (and therefore no agglomeration). When an external magnetic field is applied, the particles transition to magnetic saturation with coercive, sharp switching and are fully remanent.

Individual barcodes are added to the particles using a simple and robust lithography process and can be read optically. As described below, a robust multiplexed assay, for example a cytokine assay, using the magnetic particles has been demonstrated highlighting their potential in assay applications.

In the embodiment, lithographically fabricated magnetic particles may advantageously achieve high magnetic moment, no interparticle interaction, a large surface area for functionalization, and robust particle specific barcoding. These particles may be referred to as magnetic carriers (MCs) in view of their ability to carry both functionalization and readable information. The large surface area of the particles may advantageously provide more area for functionalisation than in conventional assay particles.

Lithographically defined magnetic nanoparticles are known in the prior art, for example in T. Vemulkar, R. Mansell, D. C. M. C. Petit, R. P. Cowburn, and M. S. Lesniak, "Highly tunable perpendicularly magnetized synthetic antiferromagnets for biotechnology applications," Appl. Phys. Lett., 2015, in H. Joisten et al., "Self-polarization phenomenon and control of dispersion of synthetic antiferromagnetic nanoparticles for biological applications," Appl. Phys. Lett., vol. 97, no. 25, p. 253112, 2010, and in S. Leulmi et al., "Comparison of dispersion and actuation properties of vortex and synthetic antiferromagnetic particles for biotechnological applications," Appl. Phys. Lett., vol. 103, no. 13, p. 132412, 2013. But in stark contrast to these lithographically defined particles and other magnetic nanoparticles in general, the MCs used here do not require the engineering of a net zero remanent magnetization state to prevent particle agglomeration. The MCs used here may optionally have net-zero remanence (and susceptibility to the generation of a magnetic moment in an external field) but despite the conventional expectation of the skilled person, they do not require net-zero remanence to avoid agglomeration. The stray field of the particles is sufficiently low to avoid agglomeration due to the shape of the magnetized material in the particle, and/or the shape of the particle, whether or not the remanent magnetization in the absence of an external field is zero.

The MCs in the embodiment are extremely high aspect ratio cuboids, with planar length and width of 40 microns, and thickness of approximately 150 nanometres.

Figure 1:
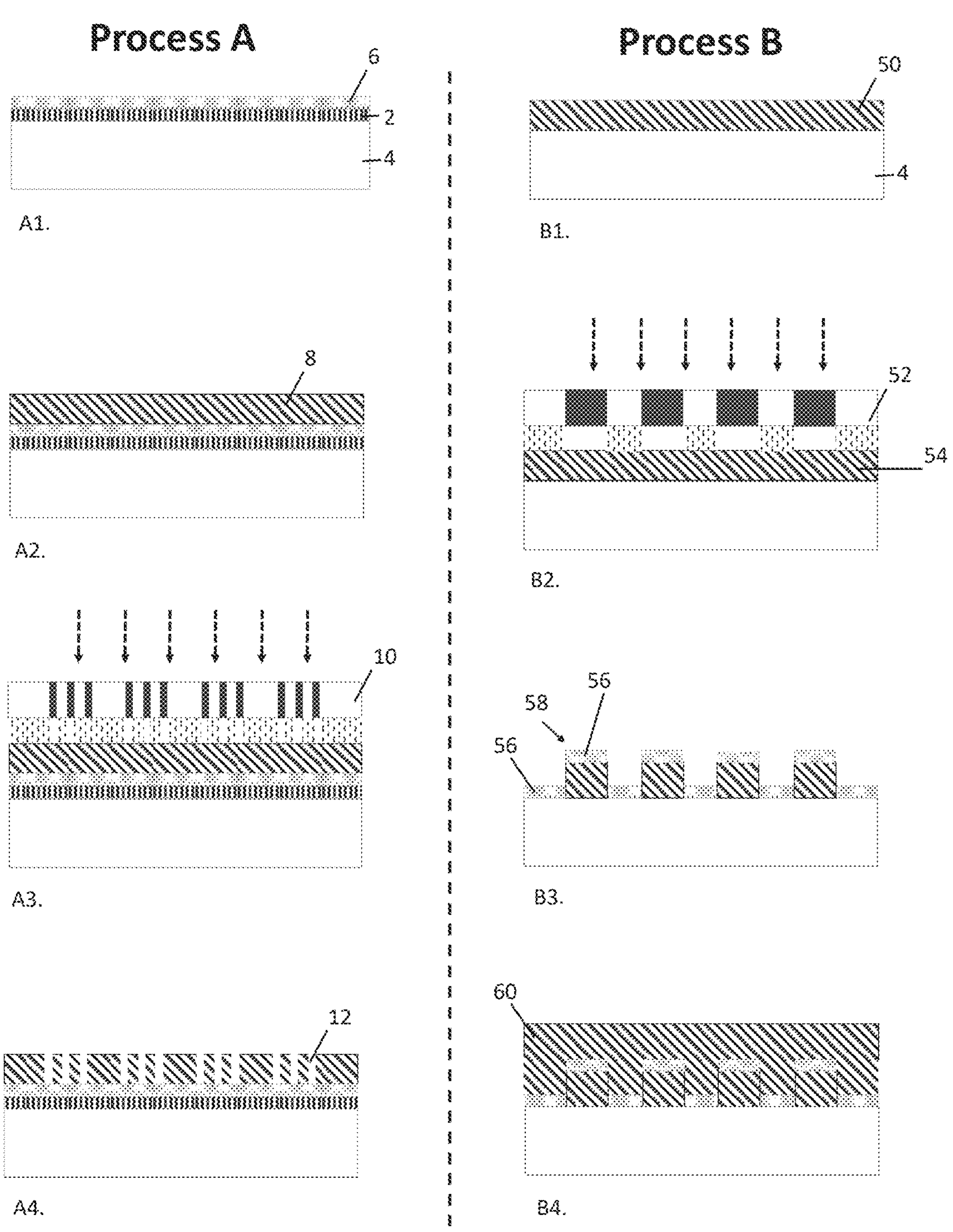
FIG. 1 illustrates steps in two processes, Process A and Process B, for the fabrication of magnetic particles according to first and second embodiments of the invention.
Figure 1:
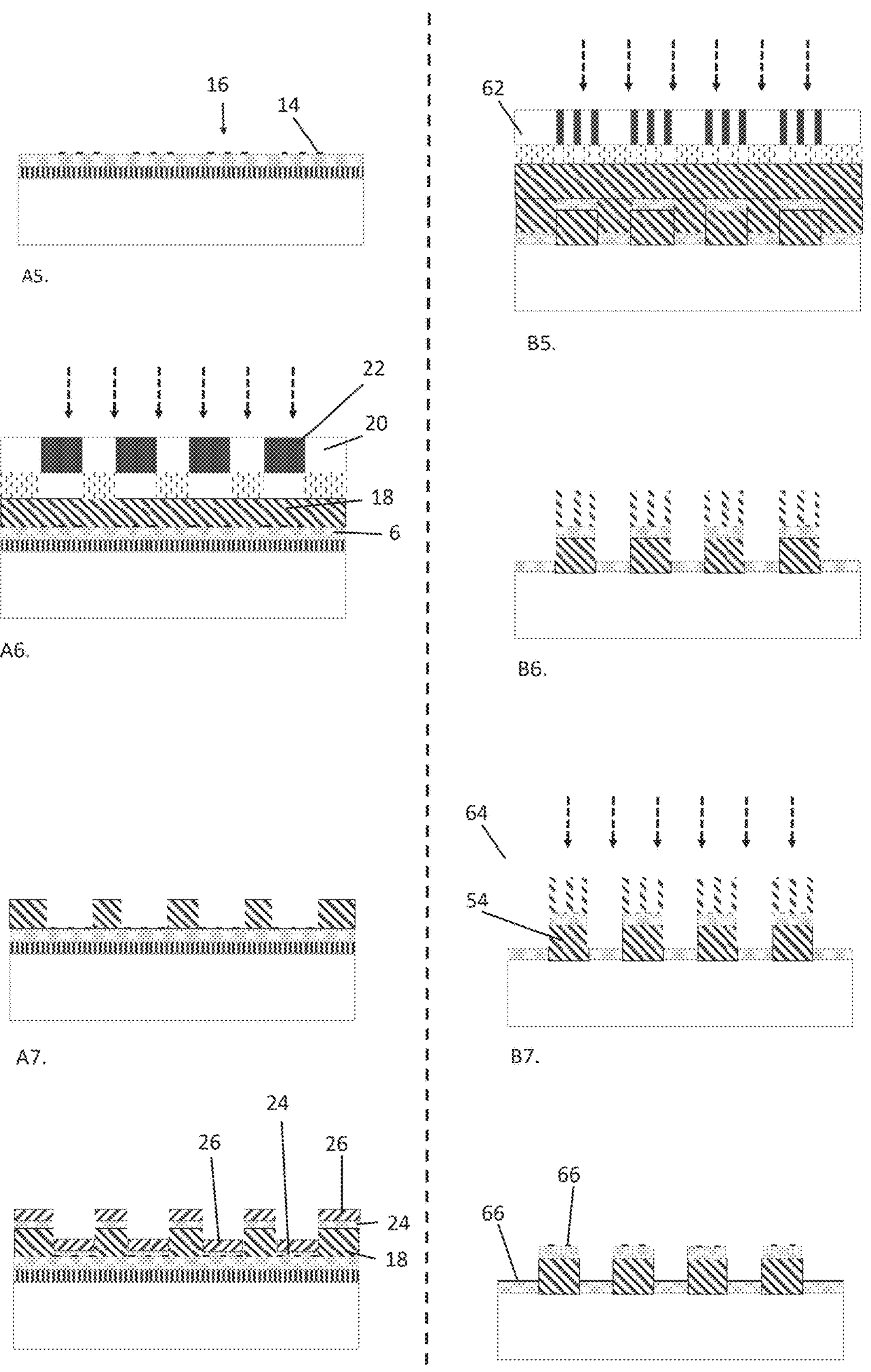
Figure 1:
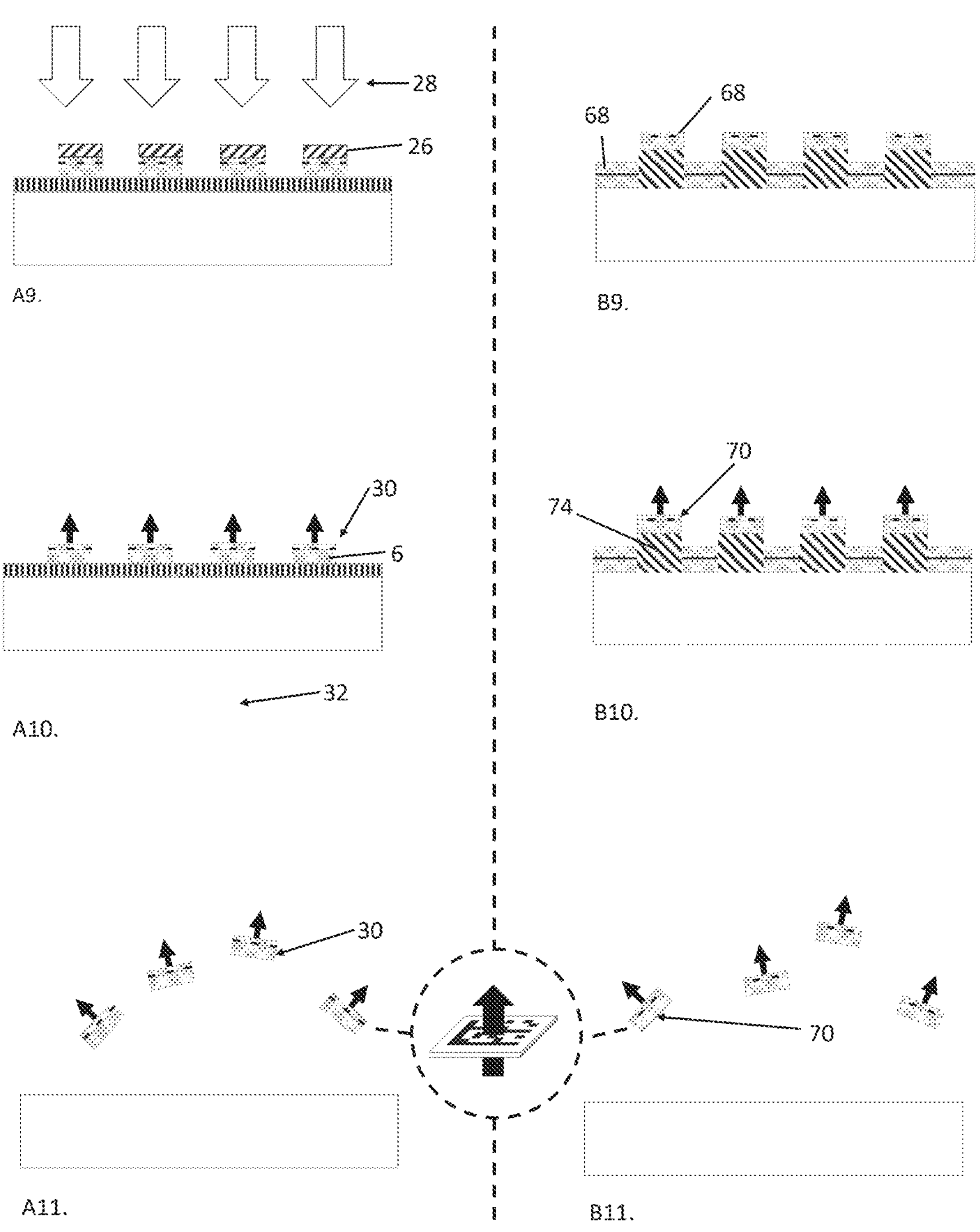

Two lithographic processes (A and B) according to two embodiments of the invention for the fabrication of magnetic particles, or MCs, are illustrated in FIG. 1.

Process A is illustrated in FIGS. 1.A1 to 1.A11. In FIG. 1.A1 a sacrificial layer 2 of 50 nm of Al is grown by magnetron sputtering on a Si substrate 4. The base 6 of the particle thin-film stack is then grown on top of this sacrificial layer, also by magnetron sputtering.

This base consists of the following 11 layers (thickness in nm): Au(100.0)/Ta(2)/Pt(4)/CoFeB(0.6)/Pt(1.2)/CoFeB(0.6)/Pt(1.2)/CoFeB(0.6)/Pt(1.2)/CoFeB(0.6)/Pt(5.0).

In FIG. 1.A2 a photoresist 8 is spin-coated over the MC base 6. The photoresist is then exposed during lithographic patterning using a photomask 10 defining the particle barcodes (or readable codes) as in FIG. 1.A3. This standard photolithography process creates a plurality of holes 12 in the photoresist illustrated in FIG. 1.A4, in which a barcode contrast material 14 such as 15 nm of Ta is deposited on top of the particle base using magnetron sputtering as shown in FIG. 1.A5. The shape and pattern of the holes defines the barcodes 16.

The photoresist is then removed in a solvent such as acetone, and a new layer of photoresist 18 is spin-coated on top of the particle base 6 and the barcodes 16 as shown in FIG. 1.A6. This is exposed in a second lithographic patterning process using a mask 20 to define the shape of the particles. In this step shown in FIG. 1.A7, the plurality of holes 22 that define the particle shape are aligned such that the barcodes are aligned at the centres of the holes.

In FIG. 1.A9 a particle (MC) cap 24, and an ion-beam-milling hard mask 26 are added by magnetron sputtering, which consist of 30-40 nm Au, and 200 nm Al respectively. The thickness of gold is selected to ensure complete coating of the particles (on both top and bottom surfaces) with Au for biocompatibility and to provide a surface for biofunctionalization. The thickness of the Au is however sufficiently thin to allow the barcode to be read through the Au layer.

In FIG. 1.A9 the photoresist 18 is then removed in a solvent such as acetone, and then the entire sample is subjected to ion-beam milling 28, a standard subtractive patterning process. Any thin film not protected by the ion-beam-milling hard mask is milled away.

Thus, the milling removes all of the thin film that forms the base of the particle thin film stack that is not within the defined particle shapes. The milling process is stopped when the sacrificial layer is reached. Any remaining Al hard mask 26 may be removed by dissolution in a 10-30 min soak in 3-5% tetramethylammonium hydroxide solution, or equivalent Al solution etchant.

Thus, photolithography patterning determines the planar shape of the particles, and the physical vapour deposition process determines their thickness and composition.

At this stage the particles 30 with barcodes, the MCs, are fully defined and lie on top of the sacrificial layer. A magnetic field 32 greater than the coercive field for the magnetic thin film of the particles is then applied to ensure that all of the particles are magnetised out-of-plane, in an "up" state, perpendicular to the top and bottom surfaces of the particles, as shown in FIG. 1.A10. Alternatively, the particles may all be magnetised in a "down" state. This links the magnetization of the particles to the physical structure of the particles in the vertical direction, allowing for alignment of the barcodes in any downstream steps such as re-deposition as shown in FIG. 3 or analysis in solution.

Finally, as shown in FIG. 1.A11, the sacrificial layer of Al beneath the particles is dissolved in an appropriate solvent to lift the particles 30 off the substrate and release them into solution in a fluid medium.

Process B is illustrated in FIG. 1.B1 to 1.B11. In FIG. 1.B1 a photoresist layer 50 is spin-coated over a Si substrate 4. It is then exposed in FIG. 1.B2 using a photomask 52 to create a plurality of islands or pillars of photoresist 54, on which a series of layers of material 56 are deposited in FIG. 1.B3 using magnetron sputtering to form the base 58 of the layered, thin-film structure of the magnetic particles. The shape of the islands or pillars defines the shape of the particles. FIG. 1.B3 thus illustrates the structure after the deposition of the first layers of the particle. These, listed from the bottom up, consist of the following thin film layers (thicknesses in nm): Au(100.0)/Ta(2)/Pt(4)/CoFeB(0.6)/Pt(1.2)/CoFeB(0.6)/Pt(1.2)/CoFeB(0.6)/Pt(1.2)/CoFeB(0.6)/Pt(5.0).

A lithographically-defined barcode is then added to the particles. As shown in FIG. 1.B4 a second layer of photoresist 60 is applied, and is exposed as shown in FIG. 1.B5 using a photomask 62 patterned with the desired barcode for each particle. In FIG. 1.B6-7 the photoresist is developed, and then flood-exposed 64 to allow for its removal in developer downstream. The bottom layer of each photoresist island or pillar 54 is shielded from this exposure step by the presence of the particles on top of the islands.

A barcode contrast material 66 such as 15 nm of Ta is grown on top of the particles in FIG. 1.B8. The top layer of photoresist is then completely removed using developer in FIG. 1.B9 and the particle cap 68 is deposited consisting of 30-40 nm of Au. The bottom layer of resist remains intact. The thickness of gold is selected to ensure complete coating of the MCs (on both top and bottom surfaces) with Au for biocompatibility and to provide a surface for biofunctionalization. The thickness of the Au is however sufficiently thin to allow the barcode to be read through the Au layer.

Thus, photolithography patterning determines the planar shape of the particles, and the physical vapour deposition process determines their thickness and composition.

At this stage, the particles with barcodes, the MCs, 70 are fully defined and lie on top of the islands of photoresist. A magnetic field 72 greater than the coercive field for the magnetic thin film of the particles is then applied to ensure that all of the particles are magnetised out-of-plane, in an "up" state, perpendicular to the top and bottom surfaces of the particles, as shown in FIG. 1.B10. Alternatively, the particles may all be magnetised in a "down" state. This links the magnetization of the particles to the physical structure of the particles in the vertical direction, allowing for alignment of the barcodes in any downstream steps such as re-deposition as shown in FIG. 3 or analysis in solution.

The thin film structure of the MCs described in this embodiment in Processes A and B is thus defined as a base of (thicknesses in nm): Au(100.0)/Ta(2)/Pt(4)/CoFeB(0.6)/Pt(1.2)/CoFeB(0.6)/Pt(1.2)/CoFeB(0.6)/Pt(1.2)/CoFeB(0.6)/Pt(5.0). A 15 nm Ta barcode is on top of this layer, and this is then capped with 30-40 nm of Au. The thinner Au at the top face allows for imaging the barcode through the Au, and thus the barcode is only visible through the top face of the particle in the embodiment described here. Thus linking the particle magnetization to the physical structure of the particle at this juncture is necessary to enable control and orientation of the barcoded face of the particle once in solution.

Finally, as shown in FIG. 1.B11, the photoresist 74 beneath the particles is dissolved in an appropriate solvent to lift the particles 70 off the substrate and release them into solution in a fluid medium.

Figure 2:
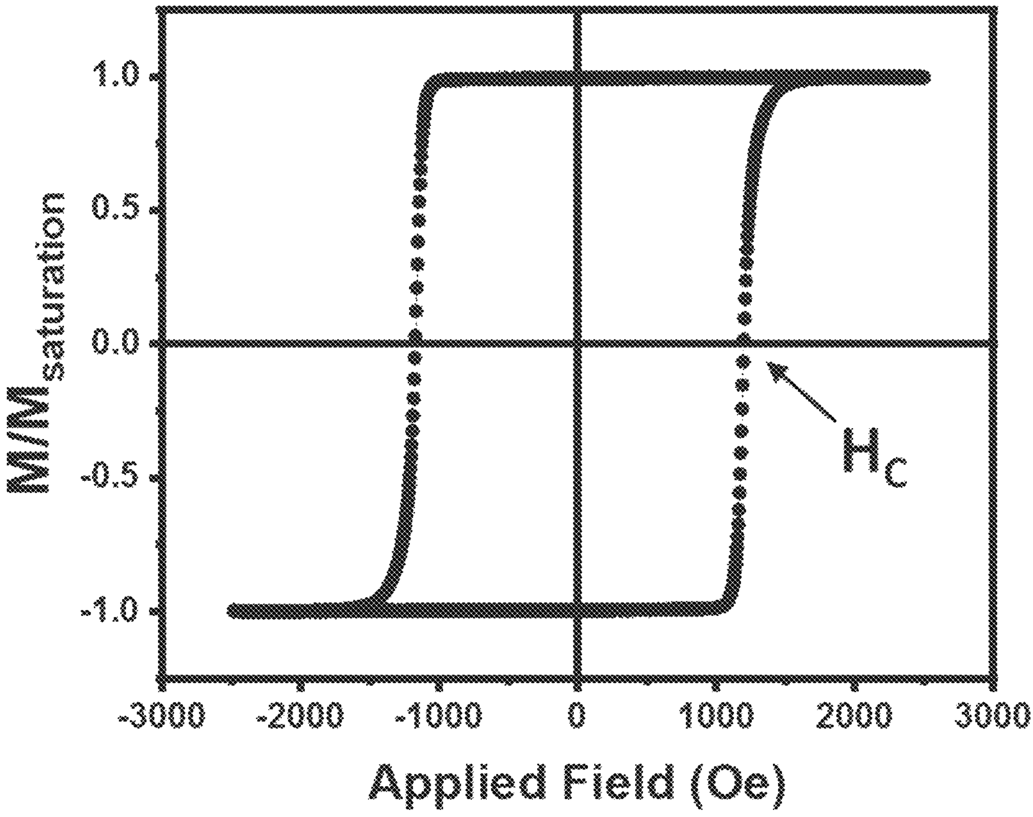
FIG. 2 is a polar magneto-optical Kerr effect (MOKE) measurement of the magnetic response of the magnetic thin film Au(100.0)/Ta(2)/Pt(4)/CoFeB(0.6)/Pt(1.2)/CoFeB(0.6)/Pt(1.2)/CoFeB(0.6)/Pt(1.2)/CoFeB(0.6)/Pt(5.0) used in the particles of the embodiments.

FIG. 2 is a polar magneto-optical Kerr effect (MOKE) measurement of the magnetic response of the magnetic thin film Au(100.0)/Ta(2)/Pt(4)/CoFeB(0.6)/Pt(1.2)/CoFeB(0.6)/Pt(1.2)/CoFeB(0.6)/Pt(1.2)/CoFeB(0.6)/Pt(5.0) used in the particles of the embodiments. The thin film magnetization is clearly out of plane with sharp, coercive magnetic switches to saturation. $H_C$ denotes the coercive field, or the field required to magnetically switch the thin film to its saturated magnetic state.

FIG. 3*a* shows how the barcode (or other 2D code) and the magnetic states of the particles 30, 70 are linked to ensure that the code may always be aligned to an external detector. First, as described above, a field above $H_C$ is used to set the magnetization of the particles in the "up" state before the particles are lifted off into solution. Once in solution, the particles will retain this magnetization state if they are not exposed to any strong magnetic field pulses. Any applied field less than $H_C$ will simply result in the particles rotating to align their magnetic moment M with the externally applied field. Field strengths from 10-1000 Oe, and frequencies from 0-50 Hz, may typically be used to control the movement of the particles. Since the barcodes are fabricated on the top surface of each particle and coated with 30-40 nm of Au through which they can be optically imaged, aligning the magnetic moment M with an external magnetic field corresponds to uniquely aligning the barcoded face of the particles in the direction of the applied magnetic (H) field. As shown in FIG. 3, the particles may thus be directed by an applied magnetic field onto a substrate, such as a planar substrate, for reading by a barcode reader and any associated detector, such as a fluorescence detector or camera.

FIG. 3*b* shows images of particles on a planar substrate and displaying readable codes such as barcodes.

FIG. 4 illustrates the stray field strength as a function of distance from the surface of a particle 30, 70 of the embodiments. It can be seen that the stray field is low, due to the high-aspect-ratio geometry of the particle. This advantageously reduces any tendency for the particles to agglomerate.

Particles according to an embodiment of the invention may be used to implement a multiplex assay as follows. Steps in the process are illustrated in FIG. 5 (*a*) and (*b*). Each particle 100 has been lithographically fabricated, for example as described above, and patterned with a barcode 102 (preferably a quick response (QR) code or 2D data matrix code. Predetermined barcodes, or other readable codes, are assigned to desired assay targets, such as particular proteins to be identified in a multichannel bioassay. Each particle carrying a code corresponding to a particular protein is then functionalised with capturing antibodies 104 specific to that respective protein as shown in FIG. 5*a*. This can be performed using conventional biochemistry protocols. The gold surfaces of the particles are suitable for this functionalisation.

In this and other embodiments, if other functionalisation of the particles is required, then materials other than gold may be used for one or both of the top and bottom surfaces of the particle. For example, $SiO_2$ may be used. Analyte detection is performed with a conventional sandwich immunoassay. When the capturing antibody captures a target protein 106, exposure of the magnetic particle to a fluorescently-labelled detection antibody 108 complementary to the capturing antibody binds to and labels the protein. As the skilled person understands, fluorescence of the fluorophore 110 in the detection antibody can then be used to indicate that the protein has been captured, and was therefore present in the sample tested in the assay.

A convenient multiplexed analyte capture platform can thus be prepared for any desired application, comprising a plurality of sets (or groups) of magnetic particles, each set of particles carrying a unique code and functionalised with the corresponding capture antibody. For a desired range of target proteins, the plurality of sets of particles corresponding to those target proteins can be mixed together in an assay sample, such as a patient sample on which a diagnosis is to be performed using a multichannel assay.

In an assay according to a preferred embodiment, illustrated in FIG. 5*b*, an analyte reagent consists of a desired set 120 of functionalised magnetic particles carried in a fluid medium 122. In a typical example, the analyte reagent may include a set or group of approximately 100-1000 coded magnetic particles (MCs) functionalised with the capturing antibody for each target protein 106. The analyte reagent is mixed with the sample to be analysed, and is allowed to react with any target proteins present. The magnetic particles are then removed from the sample and the fluid medium by magnetic separation 124. This involves attracting the particles together using an external magnetic field 126 (for example so that they gather 128 at the bottom of a container holding the sample) and the sample removed or decanted. The particles are then re-suspended in a fluid medium 130 and exposed to the corresponding fluorescently-labelled detection antibodies 108. Through the application of an external magnetic field the particles are then driven, or steered, and positioned on a surface 132 for reading. The surface may be a glass slide for example. Notably, because each particle has been magnetised out-of-plane, with the magnetisation in a unique direction towards or away from the top surface of the particle, the particles can be steered so that they are all in the same plane as each other, on the surface for reading, and so that they are all oriented in the same way, for example with the top surface of each particle facing away from the reading surface.

In an alternative embodiment, the particles may be magnetised in-plane, with the magnetic field parallel to the top or bottom surface of the particles. The particles can then be directed by the external magnetic field onto the surface for reading, but they cannot all be aligned with the top or bottom surface of each particle facing away from the surface. This apparent problem may be solved in one of two ways. The particles may be fabricated with readable information on both the top and bottom sides of the particles, so that the information may be read from either side. Alternatively, the particles may be fabricated such that the readable information can be read from either side of the particle, for example by making the particle layers sufficiently transparent that the information can be read from both the top and bottom surfaces.

Once the particles have been positioned on the surface 132 for reading, two images of the particles can be taken using suitable cameras and control software. A first image 134 is a bright field image showing the codes or information on each particle. This unambiguously identifies which of the particles in the image is carrying the capture antibody for each target protein, or in other words to which channel of the multichannel assay each particle belongs. A second image 136 is a fluorescence image of the particles. If a particle fluoresces, then the detection antibodies on that particle have captured the corresponding protein, and the fluorescence intensity may indicate the concentration of the protein in the sample. If a particle does not fluoresce, then that particle has not captured its corresponding protein, which is therefore not present in the sample. An overlay of the two images can therefore identify which proteins were present in the sample by assigning a fluorescence intensity value to each particle. Corresponding analysis software may then indicate which proteins are present in the sample, and the concentrations of those proteins. A significant feature of the multichannel analysis enabled by the barcoding of the particles is that the potential number of plex channels is extremely large, up to as many channels as can be coded by the barcodes, which may even be 1000 channels or more. At the same time, the particles in individual channels can be unambiguously identified, achieving little or no crosstalk between the channels. By comparison, conventional bead based bioassays use fluorescence-based channel identification systems which are much less resistant to crosstalk. For example, one prior art system uses ratios of fluorophores for barcoding beads, and a fluorophore-labelled antibody as the positive signalling for analyte detection. This creates challenges in reliability of channel identification and severely limits plex numbers.

The invention claimed is:

1. A method for performing an assay, comprising:

providing a magnetic particle with a functionalised surface to a liquid assay sample, in which the magnetic particle comprises a layered structure between a top surface of the magnetic particle and an opposed bottom surface of the magnetic particle, the layers including one or more magnetized layers, in which that ratio of lateral dimension of the one or more magnetized layers to a thickness or aggregate thickness of the magnetized layer or layers is greater than 500;

allowing the functionality of the magnetic particle to interact with the assay sample;

applying a magnetic field to steer the magnetic particle to a reading position; and obtaining an assay result by measuring the interaction of the functionality of the magnetic particle with the assay sample.

2. The method according to claim 1, in which the magnetic particle carries readable information, and obtaining an assay result comprises reading the readable information.

3. The method according to claim 2, in which the readable information corresponds to the functionality of said magnetic particle.

4. The method according to claim 2, in which the readable information comprises an optically readable code which is readable at or from one or both of the top or the bottom surface of the magnetic particle.

5. The method according to claim 2, in which the top or bottom surface of the magnetic particle is functionalised and in which the readable information is readable at or from the same surface as is functionalised.

6. The method according to claim 2, in which the readable information is applied to the top or bottom surface of the magnetic particle.

7. The method according to claim 1, in which the step of applying the magnetic field comprises controlling the orientation of the magnetic particle.

8. The method according to claim 1, comprising:

providing a plurality of the magnetic particles, in which each of the plurality of magnetic particles has a functionalised surface; and obtaining an assay result by measuring the interaction of the functionalities of two or more of the magnetic particles with the assay sample.

9. The method according to claim 8, comprising providing 100 or more magnetic particles.

10. The method according to claim 8, in which each magnetic particle of the plurality of magnetic particles carries readable information corresponding to the functionalisation of that magnetic particle.

11. The method according to claim 1, in which the magnetic particle is non-agglomerating.

12. The method according to claim 1, in which the functionalised surface is biofunctionalized or chemically functionalised.

13. The method according to claim 1, in which at the reading position the magnetic particle is in contact with a substrate.

14. The method according to claim 1, in which the applied magnetic field is between 0.05 T and 2 T.

15. The method according to claim 1, further comprising making the magnetic particle by a lithographic process.

16. The method according to claim 1, in which the magnetized layer or layers comprise a volume V of magnetic material having a magnetisation or average magnetisation MS, a cross section of the layer or layers has an aspect ratio AR, and $AR/Ms^2$ (with Ms measured in A/m) is greater than $8\times10^{-10}$ $(A/m)^{-2}$.

17. The method according to claim 1, in which the layers are parallel layers.

18. The method according to claim 1, in which the top and bottom surfaces of the magnetic particle are separated by a particle thickness of between 5 nm and 100 μm.

* * * * *